United States Patent [19]

Hishiki et al.

[11] Patent Number: 4,631,512

[45] Date of Patent: Dec. 23, 1986

[54] VOLTAGE DIVIDING RESISTOR DEVICE

[75] Inventors: Hideo Hishiki; Yukio Kamiyama, both of Iwai, Japan

[73] Assignee: Victor Company of Japan, Ltd., Japan

[21] Appl. No.: 616,471

[22] Filed: Jun. 1, 1984

[30] Foreign Application Priority Data

Jun. 3, 1983 [JP] Japan .............................. 58-84945[U]

[51] Int. Cl.$^4$ ........................................... H01C 10/16
[52] U.S. Cl. ......................................... 338/48; 338/123; 338/160; 338/97; 338/202; 29/610 R
[58] Field of Search ................. 338/122–128, 338/135, 160, 162, 92, 95, 97, 118, 174, 184, 202, 120, 48; 29/610 R

[56] References Cited

U.S. PATENT DOCUMENTS

| | | | |
|---|---|---|---|
| 2,883,499 | 4/1959 | Kulby et al. ................... | 338/128 X |
| 3,585,559 | 6/1971 | Rozema et al. ................ | 338/174 X |
| 3,723,938 | 3/1973 | Gramm .......................... | 338/162 |
| 3,909,769 | 9/1975 | Rozema et al. ................ | 338/48 |
| 4,225,843 | 9/1980 | Nakamura et al. ............. | 338/120 |
| 4,492,950 | 1/1985 | Simovits, Jr. .................. | 338/184 X |

FOREIGN PATENT DOCUMENTS 2028674 6/1970 Fed. Rep. of Germany ...... 338/120
2828913 2/1983 Fed. Rep. of Germany ...... 338/118

OTHER PUBLICATIONS

Vick, "Trimming Potentiometers", *International Electronics*, vol. 17, No. 5, (Sep.-Oct. 1970), pp. 28-31.

*Primary Examiner*—C. L. Albritton
*Assistant Examiner*—M. M. Lateef
*Attorney, Agent, or Firm*—Andrus, Sceales, Starke & Sawall

[57] ABSTRACT

A voltage dividing resistor device comprises a pair of electrode terminals applied with a voltage, a plurality of resistor bodies coupled between the pair of electrode terminals, an electrode terminal through which a divided voltage is obtained from an intermediate point located among the plurality of resistor bodies, and at least one conductor part formed to overlap with a part of at least one of the plurality of resistor bodies. An effective length of the resistor body which has a part thereof overlapping with the conductor part, is shortened by a length of the conductor part. The length of the conductor part is set depending on the divided voltage which is to be obtained.

9 Claims, 6 Drawing Figures

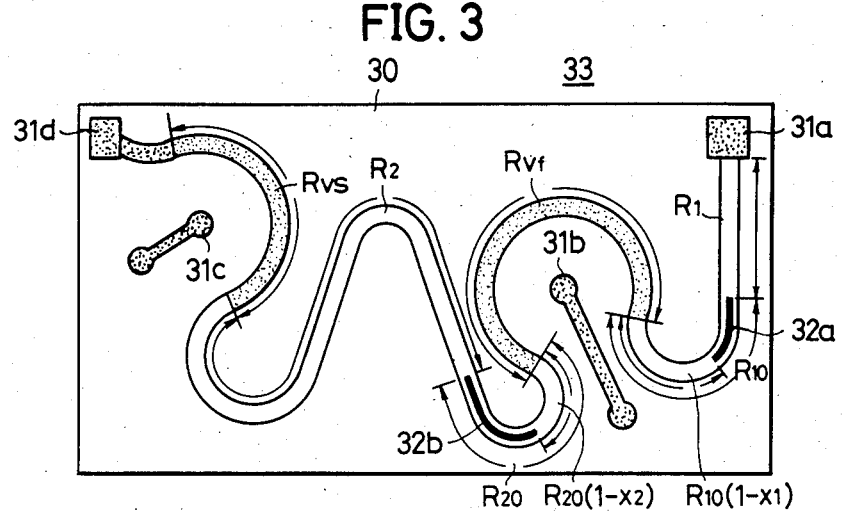
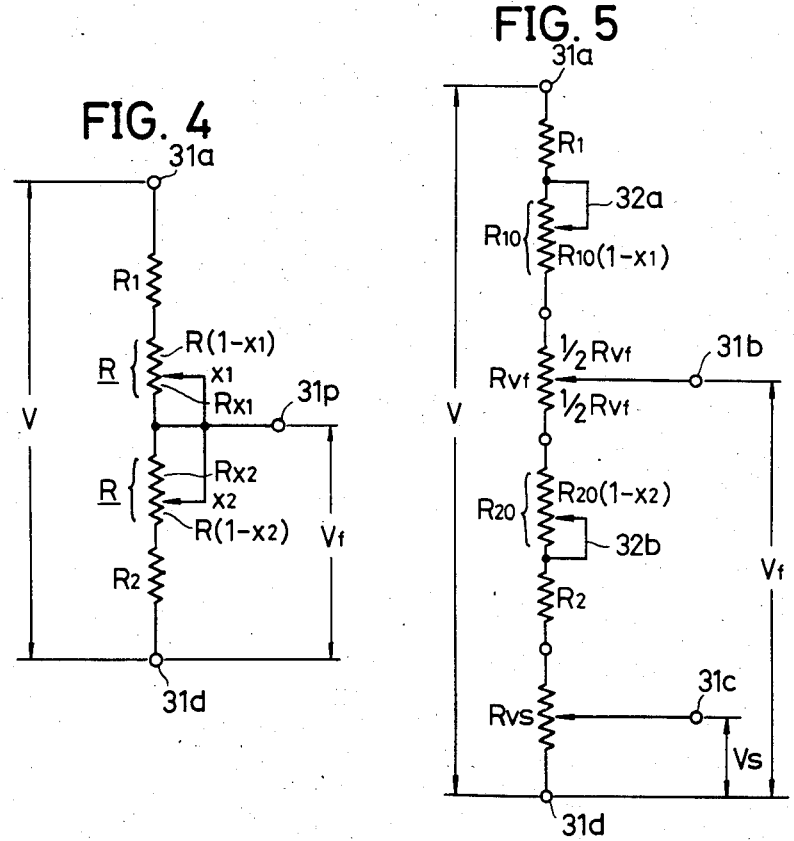

VOLTAGE DIVIDING RESISTOR DEVICE

BACKGROUND OF THE INVENTION

The present invention generally relates to voltage dividing resistor devices for dividing a voltage, and more particularly to a voltage dividing resistor device having a design such that it is easy to manufacture different types of voltage dividing resistor devices which are capable of obtaining different divided voltages.

Generally, a voltage dividing resistor device is employed in a circuit which produces a divided voltage at a high-voltage output stage of a flyback transformer in a color television receiver, for example. This voltage dividing resistor device divides a high-voltage output from a high-voltage coil of the flyback transformer, or divides an output voltage obtained from an intermediate point of the high-voltage coil, and obtains a focusing voltage $V_f$ and a screen voltage $V_s$ by use of the divided voltage.

However, the focusing voltage $V_f$ of an image receiving tube in the recent color television receiver, is usually set to a voltage which is within a range of 20% to 40% of an anode voltage $V_a$. The value of the focusing voltage $V_f$ depends on the type (or model) and the manufacturer of the color television receiver. The standard value of the focusing voltage $V_f$ is set within a range of ±2% of the design center value, and the focusing voltage $V_f$ is actually variable within a range of approximately +3% of the design center value. But since the focusing voltage $V_f$ greatly differs depending on the type of the color television receiver, even among the color television receivers of the same manufacturer, it is virtually impossible to design a voltage dividing resistor device having a large variable range so that it is possible to obtain the focusing voltage $V_f$ for each of the types of color television receivers. Accordingly, it was necessary to manufacture different types of voltage dividing resistor devices for each of the types and manufacturers of the color television receivers.

In other words, when the receiver, the type of the image receiving tube, the model or the like differ, the optimum focusing voltage $V_f$ and the screen voltage $V_s$ respectively differ. Among the image receiving tubes of the color television receivers which are presently marketed, a ratio $V_f/V_a$ between the focusing voltage $V_f$ and the anode voltage $V_a$ is generally selected to 0.24, 0.28, 0.32, and 0.38. Thus, the resistances. resistors within the voltage dividing resistor device must be selected so that the optimum ratio $V_f/V_a$ can be obtained for the image receiving tube which is to be used. On the other hand, the screen voltage $V_s$ differs depending on the operating condition of the image receiving tube, but it should be able to obtain a voltage in the range of 200 volts to 1000 volts.

However, the voltage which is applied to the voltage dividing resistor device is not constant. Especially in the case of a circuit which obtains an output voltage from an intermediate point of the high-voltage coil of the flyback transformer, the output voltage differs depending on the type of the color television receiver. Hence, a voltage dividing resistor device having a voltage dividing ratio which is dependent on the combination of the image receiving tube and the flyback transformer, had to be designed and prepared for each of the types of color television receivers.

Conventionally, when manufacturing voltage dividing resistor devices having different voltage dividing ratios, electrodes were printed by use of the same electrode pattern because the locations of terminals which are connected to the electrodes and the locations of shafts of the variable resistors are the same for each of the voltage dividing resistor devices having the different voltage dividing ratios unless the design of the device is changed. Thereafter, the resistances were set by suitably setting the ratios between lengths of resistor patterns. The resistor bodies were printed by use of a screen mask for forming the resistor pattern. The screen mask was designed so that a total resistance which is the sum of the resistances of the resistor patterns is the same for each of the voltage dividing resistor devices.

Accordingly, when manufacturing different types of voltage dividing resistor devices having different voltage dividing ratios according to the conventional method, the screen masks for forming the resistor patterns so as to obtain the resistor bodies having different resistances, were prepared for each of the types of the voltage dividing resistor devices. Hence, when manufacturing the different voltage dividing resistor devices, the screen mask for forming the resistor pattern had to be changed for each voltage dividing resistor device. In a case where the screen mask is changed to manufacture the different types of voltage dividing resistor devices, the thickness of emulsion on the screen mask, the mounting state of the screen mask on a printer, the tension in the screen mask, the inclination of the squeeze, the coefficient of viscosity of a resistor paste, or the like differ every time the screen mask is changed. Thus, a test print had to be initially made to determine whether a desired characteristic can be obtained by baking the test printed resistor bodies. Due to this necessity to make the test print and perform the checking operation to determine whether the desired characteristic can be obtained by baking the test printed resistor bodies every time the screen mask is changed, the productivity was poor. In other words, as the number of times the screen masks are to be changed increased, it took more time and manpower to perform the checking operations. Therefore, there was a problem in that the manufacturing cost of the voltage dividing resistor device became high.

SUMMARY OF THE INVENTION

Accordingly, it is a general object of the present invention to provide a novel and useful voltage dividing resistor device in which the problems described heretofore have been eliminated.

Another and more specific object of the present invention is to provide a voltage dividing resistor device in which a resistor for adjusting the voltage dividing ratio, is formed to overlap with a conductor having a length set depending on a desired voltage dividing ratio, at least at one of output terminals through which a divided voltage is produced. According to the voltage dividing resistor device of the present invention, only a conductor pattern needs to be changed and the same resistor pattern can be used when manufacturing different types of voltage dividing resistor devices having different voltage dividing ratios. Hence, it is more easy to manufacture the different types of voltage dividing resistor devices compared to the conventional method in which the resistor pattern had to be changed for each of the types of voltage dividing resistor devices. In other words, the productivity of the voltage dividing resistor device according to the present invention is high because unlike in the conventional case, it is unnecessary to make test prints and check whether a desired characteristic can be obtained by baking the test printed resistor bodies. In addition, by preparing printed circuits having conductor patterns in which the lengths of the conductors are in accordance with each of the voltage dividing ratios, it is possible to obtain the voltage dividing resistor devices having the different voltage dividing ratios by printing the same resistor pattern over the different conductor patterns. This means that printed circuits having the different voltage dividing ratios can be continuously manufactured by use of the same resistor pattern over the different conductor patterns. Accordingly, it is possible to manufacture small quantities of different voltage dividing resistor devices at a low cost. Further, according to the present invention, divided resistor bodies are made up of a plurality of variable resistors and fixed resistors which are coupled in series, and the resistor for adjusting the voltage dividing ratio is provided across the variable resistor having the higher potential. Hence, it is possible to vary the voltage dividing range of the variable resistor having the higher potential without varying the voltage dividing range of the variable resistor having the lower potential. For example, when the present invention is applied to a voltage dividing resistor device having variable resistors for adjusting the focusing voltage and the screen voltage in a color television receiver, it becomes possible to vary only the varying range of the focusing voltage, without varying the total resistance of the resistors and the adjusting range of the screen voltage.

Other objects and further features of the present invention will be apparent from the following detailed description when read in conjunction with the accompanying drawings.

BRIEF DESCRIPTION OF THE DRAWINGS

FIG. 3 is a plan view showing an embodiment of a voltage dividing resistor device according to the present invention;

FIG. 4 is a circuit diagram for explaining the principle of the voltage dividing resistor device according to the present invention; and FIG. 5 is a circuit diagram of the voltage dividing resistor device shown in FIG. 3.

DETAILED DESCRIPTION

Figure 1A:
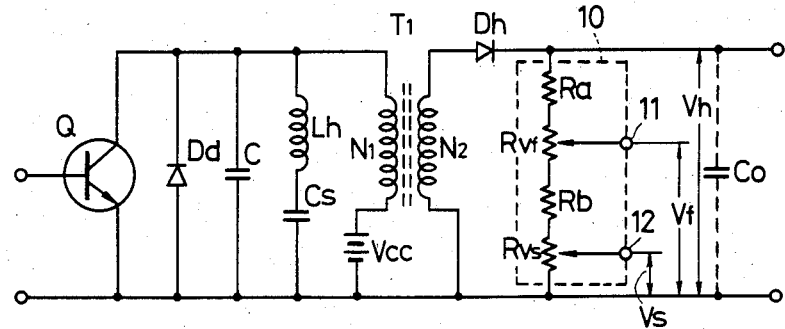
FIGS. 1A and 1B are circuit diagrams each showing an example of an output circuit of a general color television receiver having a voltage dividing resistor device.
Figure 1B:
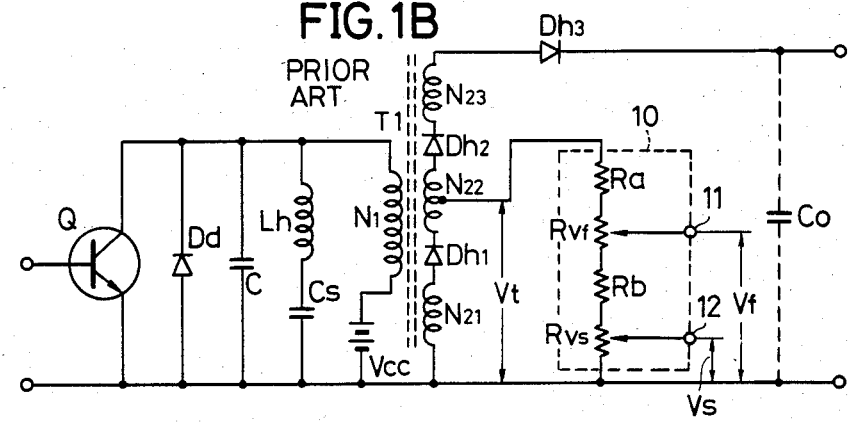

Examples of an output circuit of a general color television receiver having a voltage dividing resistor device, are shown in FIGS. 1A and 1B. In the example shown in FIG. 1A, a damping diode $D_d$, a resonant capacitor C, a horizontal deflection coil $L_h$, a capacitor $C_s$ for compensating an S-curve characteristic, and a primary coil (low-voltage coil) $N_1$ of a flyback transformer $T_1$ are coupled in parallel between a collector and an emitter of a horizontal output transistor Q. The coil $N_1$ is coupled to a power source $V_{cc}$. A rectifier $D_h$ capable of withstanding a high voltage and a voltage dividing resistor block 10, are coupled to a secondary (high-voltage coil) $N_2$ of the flyback transformer $T_1$. A capacitance $C_o$ is the capacitance of a tube wall of an image receiving tube (not shown). The voltage dividing resistor block 10 comprises fixed resistors $R_a$ and $R_b$, and variable resistors $R_{Vf}$ and $R_{Vs}$. Sliders of the variable resistors $R_{Vf}$ and $R_{Vs}$ are coupled to respective terminals 11 and 12. A high output voltage $V_h$ which is obtained from the secondary coil $N_2$, is applied to both terminals of the voltage dividing resistor block 10. A focusing voltage $V_f$ and a screen voltage $V_s$ which are obtained by voltage-dividing the voltage $V_h$, are obtained from the respective terminals 11 and 12.

In the example shown in FIG. 1B, secondary coils (high-voltage coils) $N_{21}$, $N_{22}$, and $N_{23}$ and rectifiers $D_{h1}$, $D_{h2}$, and $D_{h3}$ capable of withstanding a high voltage, are respectively coupled in series to the secondary side of the flyback transformer $T_1$. The voltage dividing resistor block 10 is coupled to an intermediate tap of the coil $N_{22}$. In this example, an output voltage $V_t$ which is obtained from an intermediate point of the coil $N_{22}$, is applied to both terminals of the voltage dividing resistor block 10.

Figure 2A:
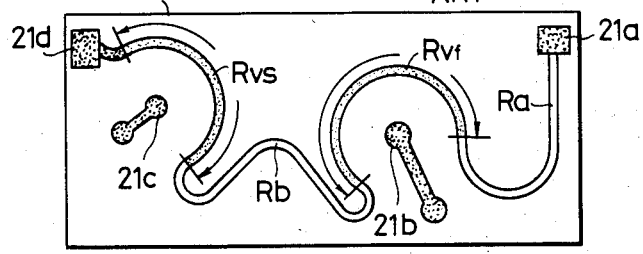
FIG. 2 is a plan view showing an example of a conventional voltage dividing resistor device.

An example of a conventional printed resistor circuit which is employed in the voltage dividing resistor block 10, is shown in FIG. 2A. Electrodes 21a through 21d are formed on a printed circuit 20. Resistors $R_a$, $R_{Vf}$, $R_b$, and $R_{Vs}$ are formed in continuance between the electrodes 21a and 21d. The resistors $R_{Vf}$ and $R_{Vs}$ have an arcuate shape about the respective electrodes 21b and 21c.

In a case where the printed circuit 20 is assembled as the voltage dividing resistor block 10, for example, two arms of a slider 25 which is made of carbon and is urged by a spring (not shown), respectively make contact with the electrode 21b and the resistor $R_{Vf}$. The slider 25 is held by a rotary body (not shown), in a state where the slider 25 is rotatable together with the rotary body which is rotated by a knob (not shown). One of the arms of the slider 25 making contact with the electrode 21b, is located coaxially of a rotary shaft of the rotary body. For this reason, when the rotary body is rotated by the knob, the slider 25 is rotated about the arm which is in contact with the electrode 21b and the other arm slides on the resistor $R_{Vf}$. The variable resistor $R_{Vs}$ has a construction similar to the construction of the variable resistor $R_{Vf}$. The constructions of the variable resistors $R_{Vf}$ and $R_{Vs}$ are known.

As described before, the optimum focusing voltage $V_f$ and the screen voltage $V_s$ differ for each of the types (or models) of image receiving tubes. Thus, in order to obtain an optimum ratio $V_f/V_a$ between the focusing voltage and an anode voltage $V_a$ for the image receiving tube which is to be used, a voltage dividing ratio $K_{vf}$ must be set so as to satisfy the following equation.

$$K_{vf}=(R_b+R_{Vs}+R_{Vf}/2)/(R_a+R_b+R_{Vs}+R_{Vf})$$

However, the voltages $V_h$ and $V_t$ which are applied to the voltage dividing resistor block 10 are not constant. Especially in the circuit shown in FIG. 1B, the output voltage $V_t$ differs depending on the flyback transformer $T_1$. Hence, it is necessary to prepare voltage dividing resistor blocks 10 having voltage dividing ratios which are dependent on the combinations of the image receiving tube and the flyback transformer.

Accordingly, when manufacturing the voltage dividing resistor devices having different voltage dividing ratios, the resistances of the resistors $R_a$ and $R_b$ had to be adjusted for each of the different voltage dividing resistor devices. In other words, the resistor pattern had to be changed for each of the different voltage dividing resistor devices. Therefore, it was necessary to prepare a plurality of kinds of resistor patterns and manufacture the different voltage dividing resistor devices by changing the screen mask of the resistor pattern. For this reason, the problems described before were introduced.

The present invention has eliminated these problems, and an embodiment of a voltage dividing resistor device according to the present invention is shown in FIG. 3. In FIG. 3, a printed resistor circuit 30 is made of a 96% alumina, for example. Electrodes 31a, 31b, 31c, and 31d are printed on the printed resistor circuit 30 by a screen mask process printing. At the same time, conductor patterns 32a and 32b which constitute an essential part of the present invention and will be described later on in the specification, are printed by the screen mask process printing. The electrodes 31a through 31d and the conductor patterns 32a and 32b are made of the same material, and silver palladium paste may be used, for example. The printed electrodes and conductor patterns are dried and then baked.

Figure 2B:
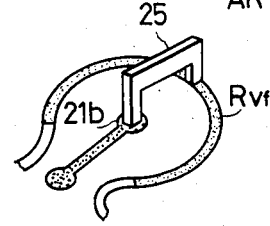

Next, continuous resistor patterns $R_1$, $R_{10}$, $R_{Vf}$, $R_{20}$, $R_2$, and $R_{Vs}$ are printed between the electrodes 31a and 31d. The lengths and the resistances of the resistor patterns $R_{10}$ and $R_{20}$ are respectively the same. Parts of the resistor patterns Rhd 10 and $R_{20}$ are formed over the conductor patterns 32a and 32b. The printed resistor patterns are then dried and baked, and a voltage dividing resistor device 33 is made by these sequence of processes. When the voltage dividing resistor device 33 is assembled as a voltage dividing resistor block, the resistor pattern $R_{Vf}$ is in contact with the electrode 31b through a first slider (not shown), and the resistor pattern $R_{Vs}$ is in contact with the electrode 31c through a second slider (not shown), as in the conventional case described before in conjunction with FIG. 2B.

First, the principle of the voltage dividing resistor device according to the present invention will be described, by referring to a simplified circuit shown in FIG. 4. In FIG. 4, an electrode terminal 31p is located between the electrode terminals 31a and 31d. The fixed resistor $R_1$ and a variable resistor R (corresponding to the resistor pattern $R_{10}$ shown in FIG. 3), are coupled between the terminals 31a and 31p. The fixed resistor $R_2$ and a variable resistor R (corresponding to the resistor pattern $R_{20}$ shown in FIG. 3), are coupled between the terminals 31d and 31p. Sliders of both the variable resistors R, are commonly coupled to the terminal 31p. The resistances of the two variable resistors R are the same, and the sliders thereof are linked. It will be assumed that a voltage V is applied across the terminals 31a and 31d, and that an output voltage $V_f$ is obtained across the terminals 31p and 31d.

It will be assumed that a ratio between a length of the resistor determined by the position of the slider with respect to the total length of the resistor, is represented by $X_1$ and $X_2$ for the two variable resistors R. In this case, the resistances of the two variable resistors R respectively become equal to $R(1-X_1)$ and $R(1 \times X_2)$. A total resistance $R_T$ can thus be described by the following equation (1).

$$R_T = R_1 + R_2 + R[(1 - X_1) + (1 - X_2)] \quad (1)$$
$$= R_1 + R_2 + R[2 - (X_1 + X_2)]$$

A voltage dividing ratio $V_f/V$ of this circuit can be described by the following equation (2).

$$V_f/V + [R_2 + R(1-X_2)]/R_T \quad (2)$$

In order to ensure that the total resistance $R_T$ is always constant, the following equation (3) must stand.

$$X_1 + X_2 + 1 \quad (3)$$

Hence, in this case, the total resistance $R_T$ can be described by the following equation (4).

$$R_T + R_1 + R_2 + R \quad (4)$$

For example, the total resistance $R_T$ is equal to 200 MΩ, and the resistances of the resistors $R_1$, $R_2$ and R for obtaining the voltage dividing ratio $V_f/V$ in a range of 0.20 to 0.40, can be calculated from the equations (2) through (4). The resistances of the resistors $R_1$, $R_2$ and R are respectively equal to 120 MΩ, 40 MΩ, and 40 MΩ. The values of the ratios $X_1$ and $X_2$ with respect to each of the values of the voltage dividing ratio $V_f/V$, can be calculated from the equations (2) and (3), and the calculated values are shown in the following table.

TABLE

| $V_f/V$ | $X_1$ | $X_2$ |
| --- | --- | --- |
| 0.20 | 0.0 | 1.0 |
| 0.24 | 0.2 | 0.8 |
| 0.28 | 0.4 | 0.6 |
| 0.32 | 0.6 | 0.4 |
| 0.36 | 0.8 | 0.2 |
| 0.40 | 1.0 | 0.0 |

From the table given above, it can be seen that in the range in which the voltage dividing ratio Vf/V assumes a value between 0.20 and 0.40, the ratios $X_1$ and $X_2$ need to be varied by 0.05, respectively, for a change of 0.01 in the voltage dividing ratio $V_f/V$.

Next, this concept is applied to the voltage dividing resistor device 33 which adjusts the focusing voltage $V_f$ and the screen voltage $V_s$ of the image receiving tube in the color television receiver. A circuit shown in FIG. 5 is equivalent to the voltage dividing resistor device 33 shown in FIG. 3. In the circuit shown in FIG. 5, a variable resistor $R_{Vf}$ is coupled between resistors $R(1-X_1)$ and $R(1-X_2)$ shown in FIG. 4, and a variable resistor $R_{Vs}$ is coupled between the resistor Rhd 2 and the terminal $31_d$ shown in FIG. 4. Further, resistors $R_{10}(1-X_1)$ and $R_{20}(1-X_2)$ are used instead of the resistors $R(1-X_1)$ and $R(1-X_2)$ shown in FIG.4.

It is possible to change the voltage dividing ratio by changing the lengths of the conductor patterns 32a and 32b in a state where the sliders of the variable resistors $R_{Vf}$ and $R_{Vs}$ assume the center position thereof, in other words, in a state where the resistances of the resistor patterns $R_1$ $R_{10}$, $R_{Vf}$, $R_{20}$, $R_2$, and $R_{Vs}$ remain unchanged and the ratio $V_s/V$ accordingly remains unchanged. It will be assumed that voltage dividing resistor blocks which are to be obtained, have three different voltage dividing ratios of 0.24, 0.28, and 0.32 shown in the table described before. In a case where the ratios $X_1$ and $X_2$ are equal to 0.2 and 0.8, respectively, the rotal resistance $R_T$ can be described by the following equation, where $R = R_{10}(1-X_1) + R_{20}(1-X_2)$.

$$R_T + R_1 + R_2 + R + R_{Vf} R_{Vs}$$

The voltage dividing ratios $V_f/V$ and $V_s/V$ of this circuit can thus be described by the following equations (5) and (6), where $X_1 + X_2 = 1$ and $R_{10} = R_{20} = R$.

$$V_f/V = [R_{Vs} + R_2 + R_{Vf}/2 + R_{20}(1-X_2)]/R_T \quad (5)$$

$$V_S V = R_{Vs}/R_T \quad (6)$$

As may be seen from the equation (5), the voltage dividing ratio $V_f/V$ can be varied by appropriately selecting the values of the ratios $X_1$ and $X_2$ in the resistances $R_{10}(1-X_1)$ and $R_{20}(1-X_2)$ so that the desired values for the frequency dividing ratio $V_f/V$ can be obtained.

In FIG. 3, the resistances of the conductor patterns 32a and 32b are negligible compared to the resistances of the resistor patterns. The lengths over which the resistor patterns $R_{10}$ and $R_{20}$ are short-circuited, varies depending on the lengths of the conductor patterns 32a and 32b. Accordingly, when the ratio of the length of the conductor pattern 32a with respect to the length of the resistor pattern $R_{10}$ is represented by $X_1$ and the ratio of the length of the conductor pattern 32b with respect to the length of the resistor pattern $R_{20}$ is represented by $X_2$, the resistance of a part of the resistor pattern $R_{10}$ which does not overlap with the conductor pattern 32a can be represented by $R_{10}(1-X_1)$, and the resistance of a part of the resistor pattern $R_{20}$ which does not overlap with the conductor pattern 32b can be represented by $R_{20}(1-X_2)$.

Therefore, it may be seen that the values of the ratios $X_1$ and $X_2$ can be selected appropriately by appropriately selecting the lengths of the conductor patterns 32a and 32b. Thus, by preparing screen masks having various lengths of conductor patterns, it is possible to obtain the desired resistances by selectively using these screen masks.

In other words, the desired frequency dividing ratios can be obtained by only changing the conductor patterns 32a and 32b, without changing the resistor patterns $R_1$, $R_{10}$, $R_{Vf}$, $R_{20}$, $R_2$, and $R_{Vs}$. When obtaining the three voltage dividing ratios of 0.24, 0.28, and 0.32 shown in the table described before, the conductor patterns 32a and 32b are designed so that the ratios $X_1$ and $X_2$ are respectively equal to 0.2 and 0.8, 0.4 and 0.6, and 0.6 and 0.4 for the three cases.

Hence, when manufacturing different voltage dividing resistor devices having different voltage dividing ratios, it is only necessary to change the patterns of the conductor patterns 32a and 32b which are printed together with the electrodes 31a through 31d. The other manufacturing processes may be the same as those employed in the conventional method described before. There is no need to change the patterns of the resistor patterns when printing the resistor bodies, and the same screen mask may be used for the screen mask process printing of the resistor patterns.

According to the present invention, it is necessary to prepare screen masks for manufacturing the various types of conductor patterns. However, it is sufficient to prepare only one kind of screen mask for the resistor pattern. That is, it is unnecessary to prepare screen masks for each of the types of resistor patterns as is required according to the conventional method. The manufacturing cost of the screen masks for the conductor patterns, is approximately 3/5 the manufacturing cost of the screen masks for the resistor patterns. As a result, the cost of the screen masks which are to be prepared is considerably low according to the present invention, and the manufacturing cost of the voltage dividing resistor device can be greatly reduced.

In the present embodiment, the voltage dividing resistor device comprises the variable resistors $R_{Vf}$ and $R_{Vs}$. However, the present invention can of course be applied to the voltage dividing resistor device comprising solely of fixed resistors. The present invention can also be applied to a voltage dividing resistor device comprising no resistor patterns $R_1$ and $R_2$. In addition, in a case where the total resistance $R_T$ does not need to be the same in the different voltage dividing resistor devices, the voltage dividing ratios may be varied by changing only one of the conductor patterns 32a and 32b so that the different resistances are obtained.

Further, the present invention is not limited to the embodiment described heretofore, but various variations and modifications may be made without departing from the scope of the present invention.

What is claimed is:

1. A voltage dividing resistor device comprising:
a substrate (30);
first through third electrodes (31a, 31b, 31d) printed on said substrate;
a group of resistor bodies ($R_{Vs}$, $R_2$, $R_{20}$, $R_{Vf}$, $R_{10}$, $R_1$) printed on said substrate, said group of resistor bodies at least comprising first through third resistor bodies ($R_{10}$, $R_{Vf}$, $R_{20}$) connected in series so that one end of said first resistor body ($R_{10}$) is coupled to said first electrode (31a) and one end of said third resistor body ($R_{20}$) is coupled to said third electrode (31d) with said decond resistor body ($R_{Vf}$) connected between said first and third resistor bodies, said first and third resistor bodies having mutually identical lengths and resistances;
a conductive member (25) coupling said second electrode (31b) with a predetermined point on said second resistor body ($R_{Vf}$), a first desired divided voltage ($V_f$) being obtained across said second and third electrodes (31b, 31d) when a predetermined voltage (V) is applied across said first and third electrodes (31a, 31d); and
first and second conductor parts (32a, 32b), at least one of which is formed to be in a mutually overlapping relationship with a part of at least one of said first and third resistor bodies ($R_{10}$, $R_{20}$), respectively,
said first and second conductor parts having lengths thereof set depending on the value of said first desired divided voltage ($V_f$) so that an equation $X_1 + X_2 = 1$ stands, where $X_1$ represents a ratio of the length of said first conductor part with respect to a length of said first resistor body and $X_2$ represents a ratio of the length of said second conductor part with respect to a length of said third resistor body,
said group of resistor bodies having a fixed total length and a fixed pattern on said substrate independent of a value of said first desired divided voltage.

2. A voltage dividing resistor device as claimed in claim 1 in which at least one of said first and second conductor parts (32a, 32b) is formed simultaneously as said first through third electrodes (31a, 31b, 31d), at least one of said first and second conductor parts being overlapped with at least one of said first and third resistor bodies ($R_{10}$, $R_{20}$), respectively.

3. A voltage dividing resistor device as claimed in claim 1 in which said conductive member comprises a movable slider (25) for coupling said second electrode (31b) with a variable point on said second resistor body ($R_{Vf}$).

4. A voltage dividing resistor device as claimed in claim 1 which further comprises a fourth electrode (31c) printed on said substrate (30) and another conductive member (25), said group of resistor bodies further comprises a fourth resistor body ($R_{Vs}$) coupled between said one end of said third resistor body ($R_{20}$) and said third electrode (31d), said other conductive member coupling said fourth electrode with a predetermined point on said fourth resistor body, a second desired divided voltage ($V_s$) being obtained across said third and fourth electrodes (31d, 31c) when the predetermined voltage (V) is applied across said first and third electrodes (31a, 31d).

5. A voltage dividing resistor device as claimed in claim 4 in which said second desired divided voltage ($V_s$) is smaller than said first desired divided voltage.

6. A method of manufacturing voltage dividing resistor devices having mutually different voltage dividing ratios, said method comprising:

(a) a step of printing at least first through third electrodes (31a, 31b, 31d) on a substrate (30);

(b) a step of printing at least one of first and second conductor parts (32a, 32b) on said substrate;

(c) a step of printing a group of resistor bodies ($R_{Vs}$, $R_2$, $R_{20}$, $R_{Vf}$, $R_{10}$, $R_1$) on said substrate, said group of resistor bodies at least comprising first through third resistor bodies ($R_{10}$, $R_{Vf}$, $R_{20}$) connected in series so that one end of said first resistor body ($R_{10}$) is coupled to said first electrode (31a) and one end of said third resistor body ($R_{20}$) is coupled to said third electrode (31d) with said second resistor body ($R_{Vs}$) connected between said first and third resistor bodies, said first and third resistor bodies having mutually identical lengths and resistances, at least one of said first and second conductor parts being in a mutually overlapping relationship with a part of at least one of said first and third resistor bodies ($R_{10}$, $R_{20}$), respectively; and (d) a step of mounting a conductive member (25) on said substrate so that said second electrode (31b) is coupled with a predetermined point on said second resistor body ($R_{Vf}$), a first desired divided voltage ($V_f$) being obtained across said second and third electrodes (31b, 31d) when a predetermined voltage (V) is applied across said first and third electrodes (31a, 31d), said group of resistor bodies being printed with a fixed total length and a fixed pattern independent of a value of said first desired divided voltage ($V_f$), said first and second conductor parts (32a, 32b) being printed with lengths thereof set depending on the value of said first desired divided voltage ($V_f$) so that an equation $X_1 + X_2 = 1$ stands, where $X_1$ represents a ratio of the length of said first conductor part with respect to a length of said first resistor body $X_2$ represents a ratio of the length of said second conductor part with respect to a length of said third resistor body.

7. A method as claimed in claim 6 in which said step (b) of printing at least one of said first and second conductor parts (32a, 32b) is performed simultaneously as said step (a) of printing at least said first through third electrodes (31a, 31b, 31d), said step (c) of printing said group of resistor bodies being performed so that at least one of said first and second conductor parts is overlapped with at least one of said first and third resistor bodies ($R_{10}$, $R_{20}$), respectively.

8. A method as claimed in claim 6 in which said step (d) of mounting said conductive member mounts a movable slider (25) for coupling said second electrode (31b) with a variable point on said second resistor body ($R_{Vf}$).

9. A method as claimed in claim 6 in which said step (a) of printing at least said first through third electrodes also prints a fourth electrode (31c) on said substrate (30), said step (c) of printing said group of resistor bodies also printing a fourth resistor body ($R_{Vs}$) on said substrate, said step (d) of mounting said conductive member also mounting another conductive member (25), said fourth resistor body ($R_{Vs}$) being coupled between said one end of said third resistor body ($R_{20}$) and said third electrode (31d), said other conductive member coupling said fourth electrode with a predetermined point on said fourth resistor body, a second desired divided voltage ($V_s$) being obtained across said third and fourth electrodes (31d, 31c) when the predetermined voltage (V) is applied across said first and third electrodes (31a, 31d).

* * * * *